United States Patent [19]

Imran

[11] Patent Number: 4,794,393

[45] Date of Patent: Dec. 27, 1988

[54] DEVICE FOR MEASURING PARAMETERS ON ELECTROCARDIOGRAM STRIP RECORDINGS

[76] Inventor: Mir A. Imran, 2707 Louis St., Palo Alto, Calif. 94303

[21] Appl. No.: 180,593

[22] Filed: Apr. 5, 1988

Related U.S. Application Data

[63] Continuation of Ser. No. 899,541, Aug. 22, 1986, abandoned.

[51] Int. Cl.$^4$ .............................................. G08C 19/10
[52] U.S. Cl. ............................. 340/870.37; 324/61 R
[58] Field of Search ................ 324/60 R, 60 C, 61 R; 340/870.3, 870.37

[56] References Cited

U.S. PATENT DOCUMENTS

| | | | |
|---|---|---|---|
| 3,221,256 | 11/1965 | Walden | 340/870.37 X |
| 4,290,065 | 9/1981 | Gleason | 340/870.37 |
| 4,303,919 | 12/1981 | Dimeff | 324/60 CX |
| 4,420,754 | 12/1983 | Andermo | 340/870.37 |
| 4,423,417 | 12/1983 | Tanaka et al. | 340/870.37 |
| 4,504,832 | 3/1985 | Conte | 340/870.37 |
| 4,543,526 | 9/1985 | Burckhardt et al. | 340/870.37 X |
| 4,566,193 | 1/1986 | Hackleman et al. | 340/870.37 X |

Primary Examiner—Ulysses Weldon
Attorney, Agent, or Firm—Flehr, Hohbach, Test, Albritton & Herbert

[57] ABSTRACT

A measuring device having first and second members mounted for cooperative movement between different positions with respect to each other. Conductors comprised of at least three groups of spaced apart elements with the elements in each group being interconnected are carried by the first member. Conductors comprised of a plurality of spaced apart elements are carried by the second member so that the conductors carried by the first member and the conductors carried by the second member face each other. A dielectric covers the conductive means on said first and second members so that at least three capacitors can be formed in serial fashion in which only one capacitor is formed in any one position of the different positions of the first and second members with respect to each other. High frequency energy is supplied to one of the conductive means so that high frequency energy can be coupled through the capacitor which is made. Electronics is coupled to the capacitor for ascertaining which capacitor has been made and for ascertaining the direction of relative movement between the first and second members and the increment of movement of the first and second members with respect to each other.

12 Claims, 5 Drawing Sheets

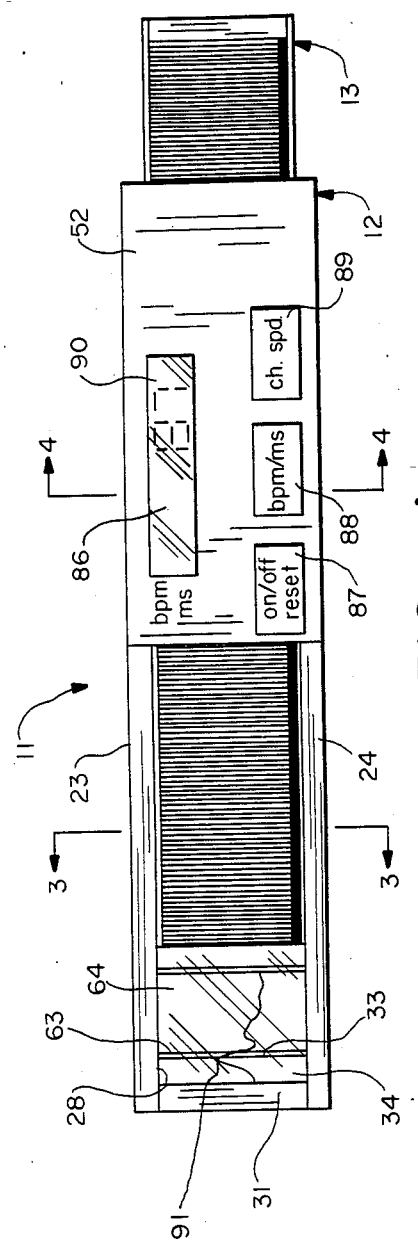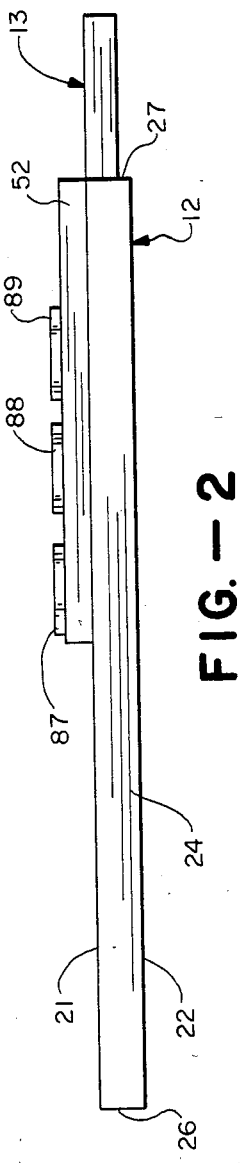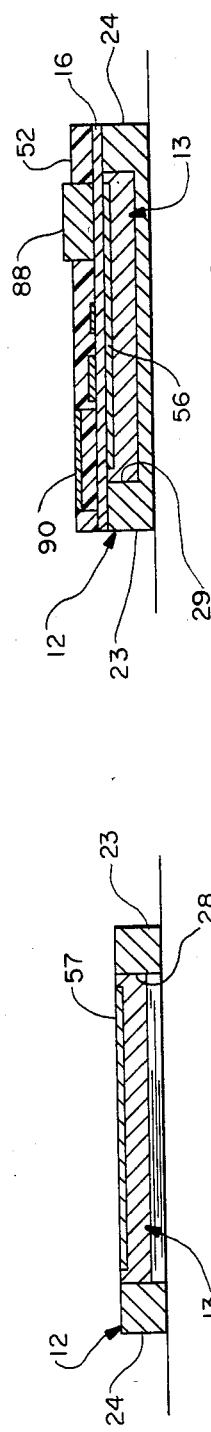

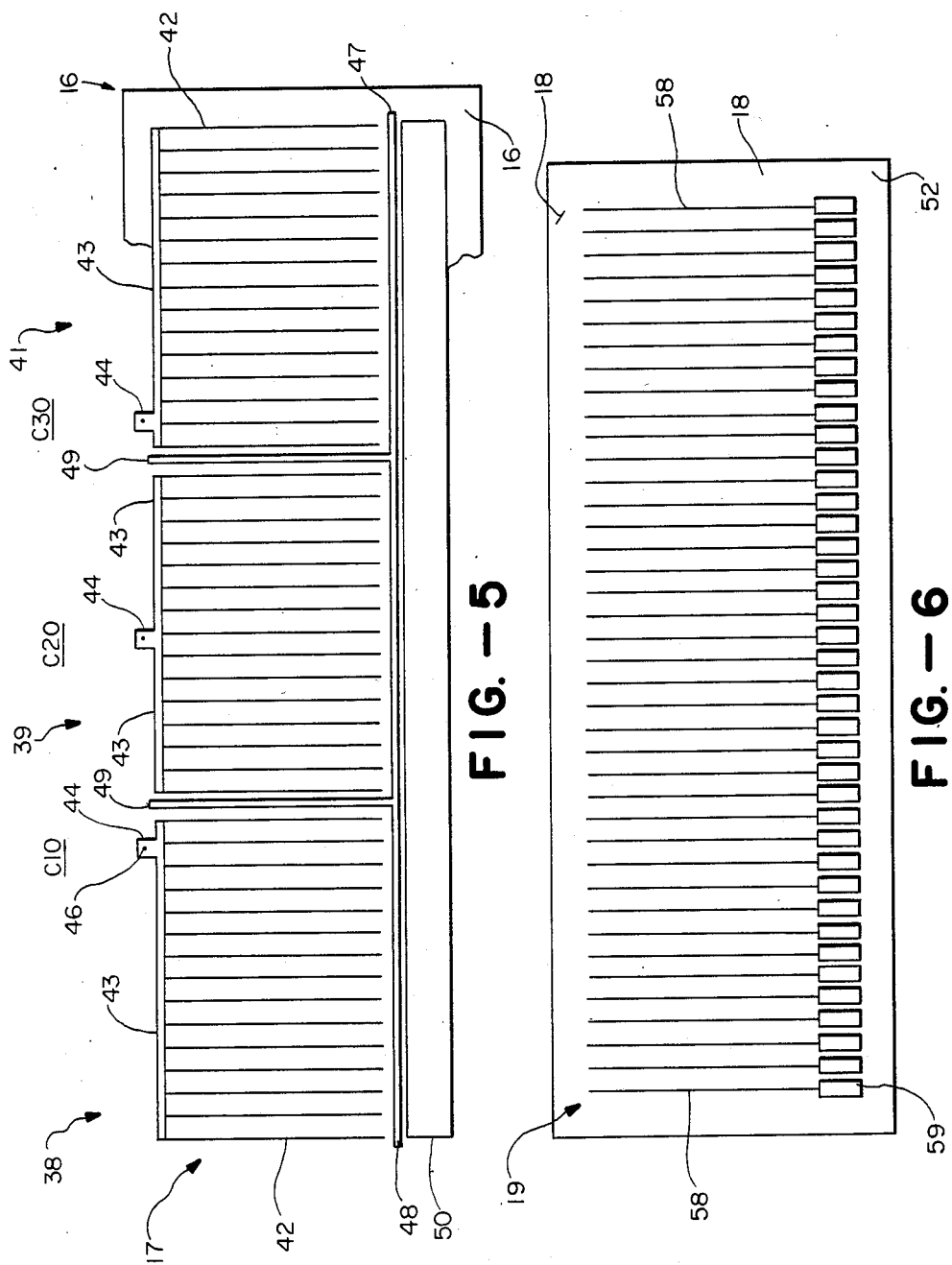

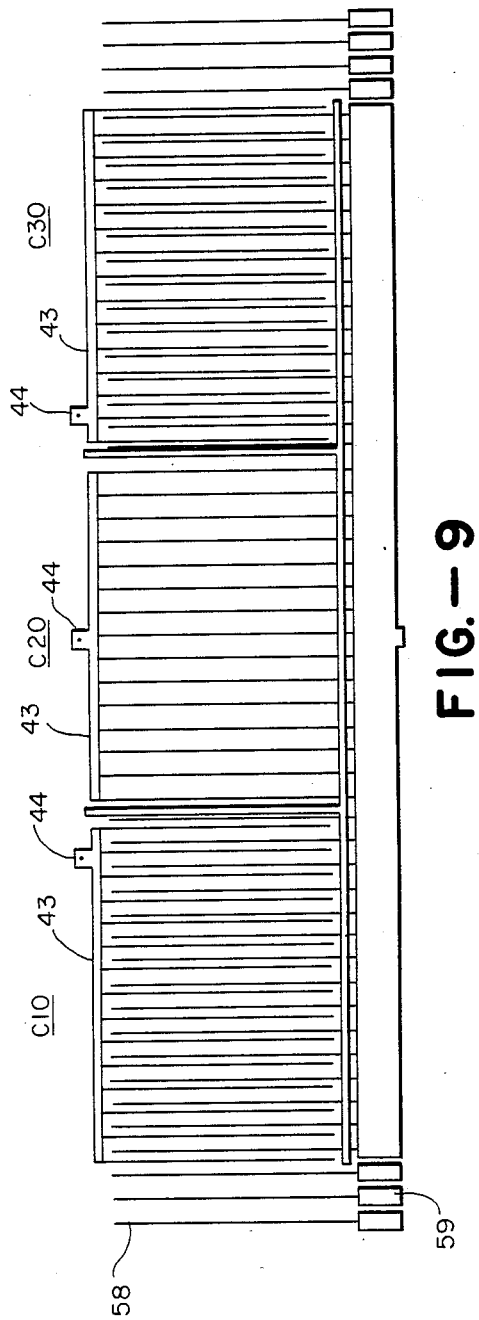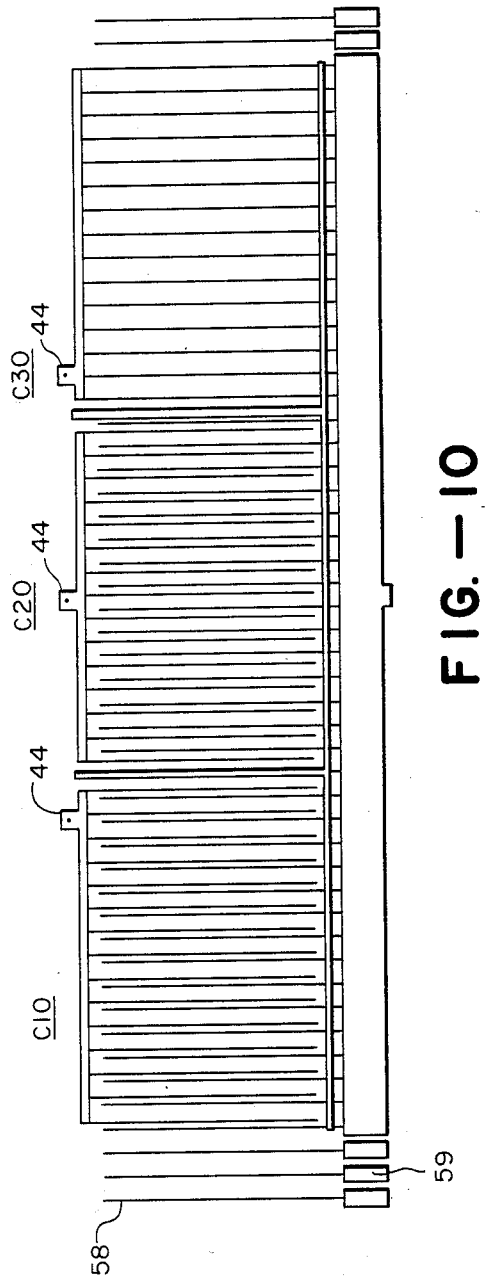

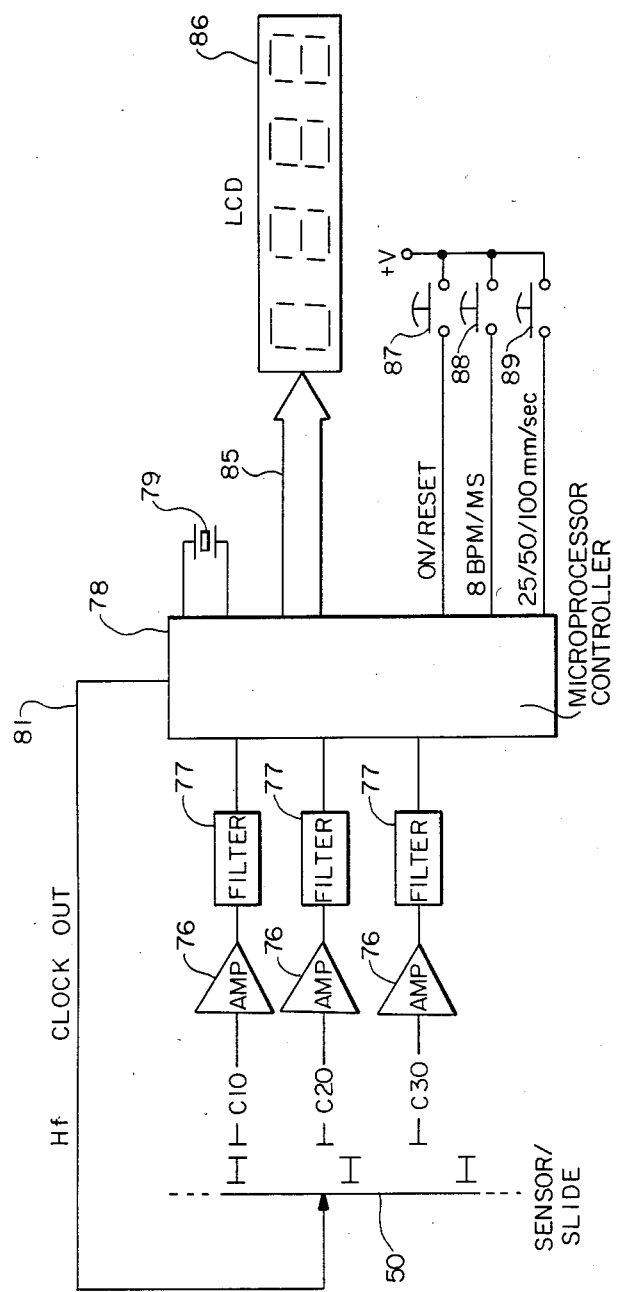
FIG.—11

DEVICE FOR MEASURING PARAMETERS ON ELECTROCARDIOGRAM STRIP RECORDINGS

This is a continuation of application Ser. No. 899,541, filed Aug. 22, 1986, now abandoned.

This application relates to a device for measuring parameters on electrocardiogram strip chart recordings and more particularly, to such a device which can be utilized by cardiologists.

In the past, for a cardiologist to carefully review an electrocardiogram to diagnose heart disease in patients, it has been necessary to utilize a pair of dividers to make measurements between two points on the electrocardiogram primarily those dealing with heart rate and beats per minute or the time duration in milliseconds between different types of waves. Typically such a procedure has utilized a divider for measuring the distance between two points and transposing this to a millimeter scale to determine the distance in millimeters. With this distance measurement a formula is used to ascertain the desired parameter. With such a procedure, error can be introduced in transposing the distance measured by the divider. In addition, such a procedure is time consuming. There is therefore a need for a new and improved device for measuring various parameters on electrocardiogram strip recordings.

In general, it is an object of the present invention to provide a device which can be utilized for measuring various parameters on electrocardiogram strip chart recordings which can be done accurately and easily.

Another object of the invention is to provide a device of the above character which utilizes electronic non-contacting measurements.

Another object of the invention is to provide a device of the above character which utilizes capacitive type coupling.

Another object of the invention is to provide a device of the above character which is in the form of a slide rule.

Another object of the invention is to provide a device of the above character which can be readily manufactured.

Another object of the invention is to provide a device of the above character which generates three separate digital signals to permit measurement of distance and direction.

Another object of the invention is to provide a device of the above character in which three capacitors are provided to generate the three signals and in which the capacitors are distributed spatially.

Another object of the invention is to provide a device of the above character which utilizes a microprocessor.

Another object of the invention is to provide a device of the above character which provides a visual display of the readings obtained.

Another object of the invention is to provide a device of the above character which is self contained.

Additional objects and features of the invention will appear from the following description in which the preferred embodiment is set forth in detail in conjunction with the accompanying drawing.

FIG. 1 is a top plan view of a measuring device for measuring parameters on electrocardiogram strip chart recording incorporating the present invention.

FIG. 2 is a side elevational view of the measuring device shown in FIG. 1.

FIG. 3 is a cross sectional view taken along the line 3—3 of FIG. 1.

FIG. 4 is a cross sectional view taken along the line 4—4 of FIG. 1.

FIG. 5 is a view of the printed circuitry utilized on the sensor board of the measuring device shown in FIG. 1.

FIG. 6 is an illustration of the printed circuitry utilized on the slide board of the measuring device shown in FIG. 1.

FIG. 9 is a drawing showing the relative positions of the sensor board and the slide board when capacitor C2 is formed.

FIG. 10 is an illustration showing the relative position of the sensor board and the slide board when capacitor C3 is formed.

FIG. 11 is a block diagram of the circuitry which is utilized in the measuring device shown in FIG. 1.

Figure 7:
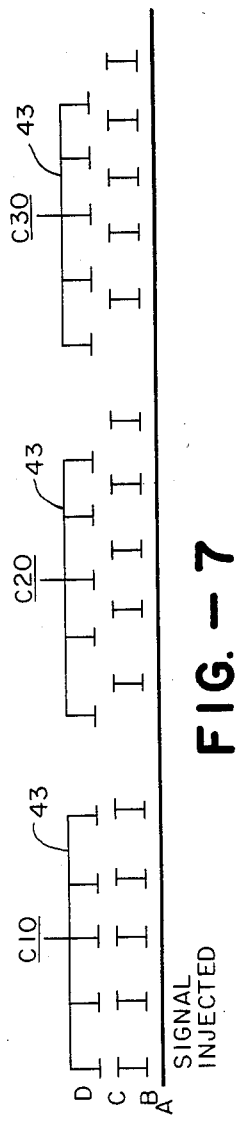
FIG. 7 is a schematic illustration of the three sets of capacitors which are formed by the printed circuitry shown in FIGS. 7 and 8.

In general the measuring device of the present invention is comprised of first and second members mounted for cooperative movement with respect to each other between different positions. Conductive means comprised of three groups of interconnected discrete elements are carried by each of the first and second members so that the conductive means carried by the first member faces the conductive means carried by the second member. Dielectric means is provided which covers the conductive means so that three capacitors are provided in which only one capacitor is formed at any one of the different positions of the first and second members. Means is provided for supplying electrical energy to the conductive means to cause at least three digital output signals to be produced as the first and second members are moved with respect to each other which can be utilized for determining the distance moved and the direction of movement between the first and second members.

More in particular, the measuring device 11 of the present invention consists of first and second members 12 and 13, formed of a suitable material such as aluminum, which are mounted for cooperative movement with respect to each other between different positions. The first member 12 is in the form of a housing which carries a sensor board 16. The sensor board 16 carries conductive means 17. The second member 13 is in the form of a slide which carries a slide board 18 which carries conductive means 19.

The housing 12 is provided with top and bottom planar parallel surfaces 21 and 22, planar and parallel side surfaces 23 and 24 which extend at right angles to the surfaces 21 and 22 and planar and parallel end surfaces 26 and 27 which also extend at right angles to the surfaces 21 and 22 and to the side surfaces 23 and 24. The housing 12 can have suitable dimensions such as 6 inches in length 1½ inches in width and ⅜ of an inch in thickness. A rectangular cutout 28 is provided which extends through the surfaces 21 and 22 as shown in FIG. 1. A recess 29 is formed in the housing 12 and extends longitudinally of the housing 12 and into the cutout 28 and receives the slide 13. The housing 12 is provided with an integral cross member 31. A cross hair 31 is disposed transverse of the opening or cutout 28 near the end of the opening or cutout 28 closest to the end of the housing 12. The cross hair 33 is supported by a plastic member 34 disposed in the opening 28 and secured to the housing 12.

The sensor board 16 which is carried by the housing 12 is formed as a printed circuit board of a suitable insulating material such as a phenolic resin. The conductive means 17 is of a suitable type, as for example, copper which is formed in a pattern on the board 16. This pattern includes three separate groups 38, 39 and 41 in which each of the groups is formed of a plurality of spaced apart discrete parallel elements or fingers 42 having a generally rectangular configuration. These fingers 42 are disposed on one surface of the board 16 and are innerconnected at one end by a conducting element 43. Each of the innerconnecting or cross conducting elements 43 is provided with a tab 44 to which an electrical connection can be made by means of a lead extending through the hole 46 provided in the tab. The three groups 38, 39 and 41 form one side or one plate of three capacitors C10, C20 and C30. The fingers 42 (see FIG. 5) form the plates D of the capacitors as shown in FIG. 7.

The conductive pattern 17 provided on the sensor board 16 also includes a ground plane 47 which serves to minimize cross talk. The ground plane consists of a conducting element 48 which extends parallel to the cross elements 43 but is disposed at the other end of the fingers 42 and is spaced therefrom. The ground plane 47 also consists of conducting elements 49 that extend at right angles to the element 48 and extend between the groups 38 and 39 and 39 and 41 respectively. Another conducting element 50 is provided parallel to the conducting element 46 and is substantially wider than the element 48 and serves as an injection bus. This bus is also identified as A in FIG. 7.

The conductive means 17 forming the pattern on the board 16 is coated with a suitable dielectric material such as a low temperature polymer to provide an insulating layer which serves two purposes. One is to provide electrical isolation for the sensor board 16 from the slide board 18 and the other is to increase the capacitance which is created between the sensor board 16 and the slide board 18. The completed sensor board 16 is mounted in the underside of a block or molding 52 of a suitable material such as plastic mounted on the housing 12 in the end which is remote from the opening 28 and is secured therein by suitable means such as an adhesive. When mounted in this manner as shown in FIG. 2, the conductive means 17 faces downwardly.

The slide board 18 is formed in a similar manner as the sensor board 16. It consists of a suitable insulating material which has the conductive means 19 provided on one surface of the same. The conductive means 19 is formed of a suitable material such as copper into a pattern as shown in FIG. 6. As shown in the pattern there are provided a plurality of spaced apart parallel fingers 58 of a generally rectangular configuration on which one end of each of the fingers 58 is connected to its own rectangular pad 59. The pad 59 are also identified with the letter C whereas the pads 59 are identified with the letter B for a purpose hereinafter described. The conducting fingers 58 can have suitable dimensions. For example, to cooperate with the dimensions of the fingers 42 shown in FIG. 7, the fingers 58 can have dimensions as, for example, 0.001 inches wide by 0.005 inches long and spaced 0.005 inches apart. The board 18 has a suitable length as, for example, approximately 6 inches.

The conductive means 19 is coated with a dielectric layer of a low temperature polymer which serves the same purpose as the dielectric layer on board 16. However, the number of fingers should be at least as great as the number of fingers on the sensor board 16. A cross hair 63 is mounted on a plastic member 64 secured to one end of the slide board 18.

The slide board 18 is mounted in the recess 29 provided in the housing 12 in such a manner so that the conductive pattern 19 faces upwardly toward the downwardly facing conductive pattern 17 of the sensor board.

The device of the present invention also includes electronics as shown in FIG. 11 in which the outputs of the capacitors identified as C10, C20 and C30 are connected through amplifiers 76 and filters 77 to a microprocessor 78. The microprocessor 78 can be of any suitable type as, for example, an 8-bit microprocessor which has 32 input/output ports. The microprocessor 78 is provided with a crystal 79 for providing a crystal-controlled output for the microprocessor 78 of a suitable frequency as, for example, 400 khz which is supplied on a clockout line 81 to the injection bus 49. As hereinafter described, this high frequency energy is capacity coupled through the capacitors to the terminals C10, C20 and C30 through the amplifiers 76 and the filters 77. The output 85 of the microprocessor is supplied to a liquid crystal display 86 which gives a display in bits per minute and milliseconds. The electronics also includes three switches 87, 88 and 89 which connect a positive source of voltage to the microprocessor and represent respectively on/reset, BPM/MS, and 25/50/100 MM per second pushbuttons. The electronics hereinbefore described can be mounted on a suitable PC board and then encapsulated within the module 52 which is secured to the sensor board 16. As shown in FIG. 1, the module 52 is provided with a window 90 through which the bits per minute and milliseconds can be read. The switches 87, 88 and 89 are mounted in such a manner that they are accessible from the top side of the block or molding 52.

The microprocessor 78 operates in two modes, "Wait" and "Stop" which are utilized to minimize the current drain on the batteries. The microprocessor is placed in the "Wait" mode automatically when the slide 13 is not moved or the functional switches 87, 88 and 89 are not depressed and placed in the stop mode when no action has occurred in approximately five minutes. Each of the switches 87, 88 and 89 controls two or more functions. The on/reset switch 87 turns the device on by waking up the microprocessor from the "Stop" mode. It is also used for resetting if an error message is displayed on the liquid crystal display 87. For example, the reset function could appear if the device is turned on when the slide 13 is not adjusted to its minimum or at home position.

Operation and use of the device for measuring parameters on electrocardiogram strip recordings may now be briefly described as follows. Let it be assumed that the slide 13 is moved to the home position shown in FIG. 1 in which the cross hairs 33 and 63 are adjacent to each other as shown therein. Let it also be assumed that with the slide rule in this home position if it is desired to make measurements on an electrocardiogram 91. The device is placed over the electrocardiogram 91 as shown in FIG. 1 with the cross hair 33 being positioned at the point on the electrocardiogram from which a measurement is to be made. As the slide 13 is moved from the position shown in FIG. 1, a 400 khz signal is generated by the microprocessor 81 which is injected into the bus bar 49. At the same time as the slide 13 is moved, the outputs of capacitors C10, C20, and C30 provide a binary pattern which the microprocessor 78 utilizes to determine distance and direction. A counter is incremented by movement of the slide 13 to the right or decrementing a counter by movement of the slide 13 to the left. An algorithm is then performed by the microprocessor on the binary contents on the counter and then displayed. The displayed value is generated by an output 85 from the microprocessor which is supplied to the liquid crystal display 86. The displayed value depends on which mode, milliseconds or beats per minute has been selected by operation of the switch 88 and the chart speed selected by operation of the switch 89. The specific operation of the capacitors C10, C20 and C30 in providing digital information for distance and direction can be readily understood by referring to FIGS. 3, 4 and 5. When the slide 13 is in the position shown in FIG. 3, capacitor C10 is being formed and the high frequency signal supplied on the bus 49 is coupled from the fingers 42 through the fingers 58 for the capacitor C10 since these are the only ones that are overlying each other. When this is the case, a signal is supplied on the output terminal C10 which causes the microprocessor 78 to realize that the capacitor C10 has been made. Further movement of the slide 13 in either direction will cause the capacitor C10 to be unmade and another capacitor either C20 or C30 to be formed. Assuming movement of the slide is to the right, the next capacitor to be formed would be C20 which causes radio frequency energy to be coupled to the output terminal C44 and to be recognized by the microprocessor 78. If the slide 13 is moved in the opposite direction, the capacitor C30 would be formed and a signal would be supplied on the output terminal 44 which would be recognized by the microprocessor. Thus, only one capacitor of the three capacitors is formed at any one relative position of the slide 13 and the housing 12 of the different relative positions which can be assumed by the slide 13 and the housing 12.

Figure 8:
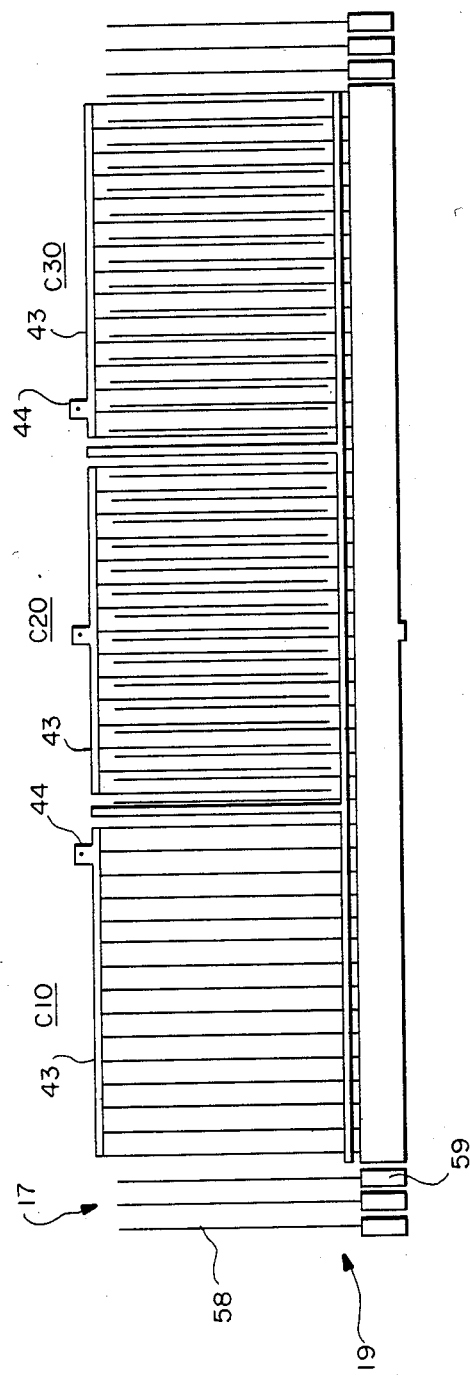
FIG. 8 is an illustration showing the relative positions of the sensor board and the slide board to form capacitor C1.

In viewing FIGS. 8, 9, and 10 it can be seen that in FIG. 8, the capacitor C10 is formed and the capacitors C20 and C30 are not formed. When the slide is moved to the left, capacitor C20 is formed and C10 and C30 are not formed. When the slide is moved further left, the capacitor C30 is formed and C10 and C20 are not formed. During this forming and unforming or making and unmaking of the capacitors in serial fashion, a signal is injected on the injection bus 49 through the pads 59 and then coupled back to the capacitors, either C10, C20 or C30 to the microprocessor 78. With this information the microprocessor 78 can ascertain the direction of travel and the distance travelled. The resolution of the distance in measurement is directly proportional to the distance between the fingers and the slide and on the slide board and the sensor board.

More particularly, when the capacitor C10 fingers 42 the sensor board overlie the fingers 58 the slide board, the signal which is injected at point A as shown in FIG. 3 is then capacitively coupled to point C. This signal is also at point C at this time and is then capacitively coupled to point D and then detected at terminal 44 of C10 of the microprocessor 78. When the slide 13 is in this position, the fingers of the slide board 18 for the capacitors C20 and C30 are not aligned with the fingers of the sensor board 16 capacitors C20 and C30 and for that reason the capacitors C20 and C30 are not formed. The forming or making of the capacitors so that distance and resolution can be defined is set forth in the table below:

| Distance | C10 | C20 | C30 | |
|---|---|---|---|---|
| | 1 | 0 | 0 | Initialize |
| .02" | 0 | 1 | 0 | Slide moved to right .02" |
| .04" | 0 | 0 | 1 | Slide moved to right .02" |
| .02" | 0 | 1 | 0 | Slide moved to left .02" |
| 00 | 1 | 0 | 0 | Slide moved to left .02" |

With distances identified in the table of maximum resolution is 0.020 inches. This resolution can be increased or decreased by increasing or decreasing the width and spacing of the conductors both on the sensor board and the slide board. Any number of conductors can be arranged to achieve the desired resolution.

By way of example, the device can give an output of 1 millimeter when the slide is in the closed position which is equal to 40 milliseconds at 25 millimeters per second which is equal to 1476 per minute. Thus it can be seen that merely by moving the cross hair of the slide from one position to another, the distance moved by the slide can be readily ascertained and the direction it has been moved can be ascertained to supply a reading in either bits per minute or in milliseconds in the digital readout 86. Different chart speeds can be utilized with the device without any difficulty.

Another embodiment of this device can be used for measuring electroencephalograms (EEG) and electromylograms (EMG). Typically EEG and EMG measurements are made in terms of "cycles per second", as opposed to "beats per minute" or "milliseconds". Consequently, the BPM/MS switch, in this embodiment is eliminated and the device only displays cycles per second. The method of operation remains the same.

It should be appreciated that the device of the present invention can be utilized in many other distance applications as, for example, measuring distance on maps and the like. This device utilizes a totally non-contacting scheme and has very low power requirements. It is very accurate because it creates digital pulses with movement of the slide which eliminates the necessity for analog to digital conversion and the drift normally associated with analog-type instruments.

From the foregoing it can be seen that there has been provided a device which makes it possible to make non-contacting measurements utilizing capacitive coupling. The device is self-contained and can be readily manufactured. Measurements can be made rapidly and with great accuracy.

What is claimed is:

1. In a measuring device, first and second members mounted for cooperative movement between different positions with respect to each other, conductive means comprised of at least three groups of spaced apart elements with the elements in each group being interconnected and carried by the first member, a single injection bus carried by the first member and spaced apart from the three groups of spaced apart elements, conductive means comprised of a plurality of spaced apart discrete elements carried by the second member so that the conductive means carried by the first member and the conductive means carried by the second member face in directions towards each other, dielectric means covering said conductive means on said first and second members so that at least three capacitors can be formed in serial fashion in which only one capacitor is formed in any one position of the different positions of the first and second members with respect to each other, oscillator means for supplying a single phase, single frequency high frequency signal to said single injection bus, said single injection bus serving to capacitively couple said high frequency signal into the discrete elements carried by the second member, the discrete elements carried by the second member serving to capacitively couple said high frequency signal into one of the groups of the elements carried by the first member to provide a discrete signal as each capacitor is made, and electronic means coupled to the capacitors for ascertaining which capacitor has been made and thereby ascertaining the direction of relative movement between the first and second members and the increment of movement of the first and second members with respect to each other.

2. A device as in claim 1 wherein the conductive means for the second member includes pads connected to each of the discrete elements and disposed opposite the single injection bus and wherein the single high frequency signal is injected from the injection bus to the pads and from the discrete elements on the second member to the one of the groups of spaced apart discrete elements on the first member.

3. A device as in claim 2 wherein said conductive means on said first member includes conducting elements disposed between the groups of members to minimize cross talk between the capacitors.

4. A device as in claim 1 together with a housing pad a slide slidably mounted in the housing and wherein said first member is carried by the housing and wherein said second member is carried by the slide.

5. A device as in claim 4 wherein the housing is provided with an opening therein and wherein the housing is provided with a cross hair which extends across the opening and in a predetermined position in the opening and wherein said slide includes a cross hair carried by the slide and wherein the slide is movable through the opening so that its cross hair can be moved relative to the position of the cross hair in the opening in the housing and still be visible through the opening in the housing.

6. A device as in claim 1 wherein said oscillator means for supplying said high frequency signal includes means for generating a radio frequency signal of a predetermined frequency, means for analyzing each of the capacitors to ascertain which capacitor has been formed and means for ascertaining the direction of movement of the first and second member with respect to each other and the distance moved by the first and second members with respect to each other.

7. A device as in claim 6 together with means for visible display of the measurements made.

8. A device as in claim 1 which is capable of being utilized for making measurements on electrocardiogram strip chart recordings, and wherein said means for supplying high frequency energy and said means for analyzing the capacitors includes a microprocessor together with switch means for selecting modes of operation for the microprocessor.

9. A device as in claim 1 wherein said electronic means includes switch means for selecting beats per minute and milliseconds and the chart speed.

10. In a measuring device for measuring parameters on electrocardiogram strip chart recording, a housing having a first opening extending therethrough and extending longitudinally of the housing, a slide slidably mounted in said housing and having one end thereof movable through said opening in said housing and movable longitudinally in the opening in the housing, conductive means carried by the housing, additional conductive means carried by the slide, dielectric means covering said conductive means, said conductive means on said housing and said conductive means on said slide facing each other, said conductive means on said housing and on said slide being formed so that at least three capacitors can be formed as said slide is moved relative to said housing in said opening in the housing but in which only one capacitor can be formed in any one position of said slide relative to said housing, a single injection bus carried by the housing adjacent the conductive means carried by the slide, electronic circuit means carried by the housing, said electronic circuit means including means for generating a single phase, single frequency radio frequency signal and supplying the same to said injection bus carried by the housing and means connected to the conductive means carried by the housing to ascertain which capacitor is made as the slide is moved relative to said housing in any one position of said slide to ascertain the direction of movement of the slide with respect to the housing and the distance moved by the slide with respect to the housing.

11. A device as in claim 10 wherein said electronic means includes digital readout means for displaying information ascertained.

12. A device as in claim 10 together with switch means for selecting desired parameters.

* * * * *